(12) United States Patent
Lowe et al.

(10) Patent No.: US 7,402,441 B2
(45) Date of Patent: Jul. 22, 2008

(54) METHOD OF DETECTING AN ANALYTE IN A FLUID

(75) Inventors: Christopher Robin Lowe, Cambridge (GB); Colin Alexander Bennett Davidson, Cambridge (GB); Jeffrey Blyth, Cambridge (GB); Satyamoorthy Kabilan, Cambridge (GB); Alexander James Marshall, Cambridge (GB); Blanca Madrigal Gonzalez, Cambridge (GB); Anthony Peter James, Cambridge (GB)

(73) Assignee: Smart Holograms Limited, Cambridge (GB)

(*) Notice: Subject to any disclaimer, the term of this patent is extended or adjusted under 35 U.S.C. 154(b) by 262 days.

(21) Appl. No.: 10/509,782

(22) PCT Filed: Apr. 4, 2003

(86) PCT No.: PCT/GB03/01499

§ 371 (c)(1),
(2), (4) Date: Oct. 21, 2005

(87) PCT Pub. No.: WO03/087899

PCT Pub. Date: Oct. 23, 2003

(65) Prior Publication Data
US 2006/0166350 A1     Jul. 27, 2006

(30) Foreign Application Priority Data
Apr. 5, 2002   (GB) ................................ 0207944.0

(51) Int. Cl.
*G01N 33/543*   (2006.01)

(52) U.S. Cl. .......................... 436/518; 422/55; 422/57; 422/58; 422/82.05; 422/82.11; 435/287.1; 435/287.2; 435/288.7; 435/808; 436/164; 436/165; 436/524; 436/527; 436/805

(58) Field of Classification Search ...................... None
See application file for complete search history.

(56) References Cited

U.S. PATENT DOCUMENTS

| 5,352,582 A | * | 10/1994 | Lichtenwalter et al. ......... 435/6 |
| 5,989,923 A | * | 11/1999 | Lowe et al. .................. 436/518 |
| 6,180,288 B1 | | 1/2001 | Everhart et al. |
| 6,198,869 B1 | | 3/2001 | Kraus et al. |

FOREIGN PATENT DOCUMENTS

| JP | 11-147059 | 6/1999 |
| WO | WO 95/26499 A1 | 10/1995 |

OTHER PUBLICATIONS

Spooncer, R.C., F.A. Al-Ramadhan and B.E. Jones (1992) "A humidity sensor using a wavelength-dependent holographic filter with fibre optic links" *Internatinal Journal of Optoelectronics* 7(3):449-452.

* cited by examiner

*Primary Examiner*—Christopher L Chin
(74) *Attorney, Agent, or Firm*—Saliwanchik, Lloyd & Saliwanchik

(57) ABSTRACT

A method for the detection of an analyte in a fluid, comprising contacting the fluid with a holographic element comprising a medium and a hologram disposed throughout the volume of the medium, wherein an optical characteristic of the element changes as a result of a variation of a physical property occurring throughout the volume of the medium, wherein the variation arises as a result of interaction between the medium and the analyte, and wherein the reaction and the variation are reversible; and detecting any change of the optical characteristic.

14 Claims, 7 Drawing Sheets

Figure 1:
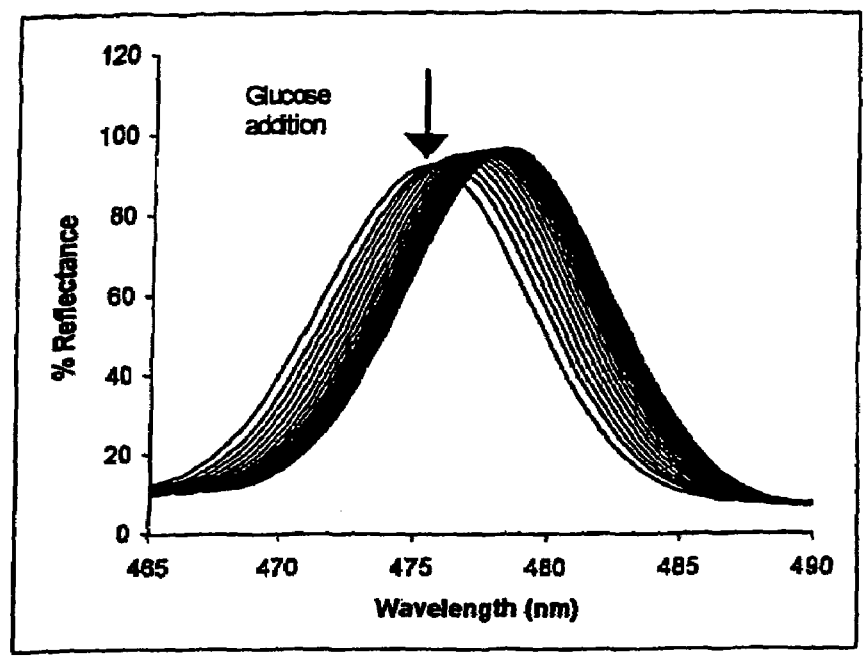

This shows how the gratings taken from the 3 cyclodextrine derivatives respond to low concentrations of for example anthraquinone 2 carboxylic acid Na salt at pH 7.5 at $30^{\circ}C$ This compares the responses of alpha CD polymer and gamma CD polymer to low levels of 4-nitro phenol sodium salt at pH 7.5 at 30°C.

Gratings could be cleared of analyte by rinsing in deionized water or buffer solution. Typically a grating was agitated in the solution in a petri dish for 30 mins and the water was changed 3 times.

Calibration of polyHEMA hologram in grape juice cotaining varying concentrations of ethanol Production of ethanol by *Saccharomyces cerevisiae* cultured in grape juice over 23 hours.

ically, to sense two independent events/
METHOD OF DETECTING AN ANALYTE IN A FLUID This application is a National Stage Application of International Application Number PCT/GB03/01499, filed Apr. 4, 2003; which claims priority to United Kingdom Application No. 0207944.0, filed Apr. 5, 2002.

FIELD OF THE INVENTION

This invention relates to a method of detection based on a sensitive element which is a hologram, and a device for use in such a method.

BACKGROUND TO THE INVENTION

A short communication to the International Journal of Optoelectronics 7(3):449-452 (1992), by Spooncer et al, entitled "A humidity sensor using a wavelength-dependent holographic filter with fibre optic links", describes the response of gelatin-based Bragg reflection holograms to ambient humidity. It concludes that optical response to an increasing and decreasing cycle of humidity shows a hysteresis which limits its industrial application as a sensor.

WO-A-9526499 discloses a holographic sensor, based on a volume hologram. This sensor comprises an analyte-sensitive matrix having an optical transducing structure disposed throughout its volume. Because of this physical arrangement of the transducer, the optical signal generated by the sensor is very sensitive to volume changes or structural rearrangements taking place in the analyte-sensitive matrix as a result of interaction or reaction with the analyte. For example, a sensor comprising a gelatin-based holographic medium may be used to detect trypsin. Trypsin acts on the gelatin medium, irreversibly destroying the integrity of the holographic support medium.

SUMMARY OF THE INVENTION

According to one aspect of the invention, a method for the continuous detection of an analyte in a fluid, comprises contacting the fluid with a holographic element comprising a medium and a hologram disposed throughout the volume of the medium, wherein an optical characteristic of the element changes as a result of a variation of a physical property occurring throughout the volume of the medium, wherein the variation arises as a result of interaction between the medium and the analyte, and wherein the reaction and the variation are reversible; and monitoring the optical characteristic.

The variation arises as a result of interaction between the medium and the analyte, wherein the interaction and the variation are reversible. The interaction may be a chemical or biochemical reaction. Since both the interaction and the reverse interaction can occur, an analyte species can be continuously detected, preferably in real time. The analyte concentration may change, while the fluid is static. Alternatively, the fluid may be passed continuously over the element.

The invention may be used to monitor a reaction in vivo or in vitro, e.g. in a fermenter. It can be used for kinetic measurement, and as an effective control system.

Another aspect of the invention is a device for the detection of an analyte in a fluid. The device comprises a sensor comprising the holographic element, and an inlet and outlet which allow the fluid to be brought into contact with, or passed over, the holographic element. The device also includes a window for non-ionising radiation to irradiate the holographic element. A reaction occurring in the element can thus be observed.

DESCRIPTION OF PREFERRED EMBODIMENTS

The interaction between the holographic support medium and the analyte is reversible, and therefore continuous detection of the analyte may be achieved. When the fluid is in contact with the holographic element, the analyte and support medium interact, preferably by a chemical or biochemical reaction. If the fluid passes over the element, the interaction may be transient.

The interaction can be detected remotely, using non-ionising radiation. The extent of interaction between the holographic medium and the analyte species is reflected in the degree of change of the physical property, which is detected as a variation in an optical characteristic, preferably a shift in wavelength of non-ionising radiation.

The property of the holographic element which varies may be its charge density, volume, shape, density, viscosity, strength, hardness, charge, hydrophobicity, swellability, integrity, cross-link density or any other physical property. Variation of the or each physical property, in turn, causes a variation of an optical characteristic, such as polarisability, reflectance, refractance or absorbance of the holographic element.

The hologram may be disposed on or in, part of or throughout the bulk of the volume of the support medium. An illuminating source of non-ionising radiation, for example visible light, may be used to observe variation(s) in the, or each, optical characteristic of the holographic element.

More than one hologram may be supported on, or in, a holographic element. Means may be provided to detect the or each variation in radiation emanating from the or each hologram, arising as a result of a variation in the or each optical characteristic. The holographic elements may be dimensioned and arranged so as to sense two independent events/species and to affect, simultaneously, or otherwise, radiation in two different ways. Holographic elements may be provided in the form of an array.

Different types of hologram exist. One or more of these may be produced in, or on, the holographic support medium. Some different types of hologram are described below.

A holographic element with the properties of a "phase" hologram may comprise a 3-D distribution (modulation) of refractive index where the distribution is a physical record of the original interference pattern. A holographic element with the properties of an "amplitude" hologram comprises a 3-D distribution (modulation) of a radiation-refracting material wherein the distribution is a physical record of an original interference pattern. Peaks of the modulation are referred to as fringes. A hologram can have the properties of a "phase" and/or an "amplitude" hologram.

The radiation may experience a phase shift as a result of modification to the distribution of index of refraction arising from a change in spacing between peaks of a distribution supported in part, or throughout the volume of, the support medium. A change in fringe separation may be measured by peak (Bragg) wavelength change at a fixed angle of incidence/diffraction, by monochromatic intensity change at a fixed angle, or by an angle change at monochromatic peak intensity.

Holograms can be further categorised into four distinct types which can co-exist in the same support medium. These are transmission, reflection, edge-lit and surface holograms. There are also evanescent-wave holograms.

A "transmission" hologram is one where the emergent rays leave the holographic support medium via the surface opposite to that by which incident rays enter. Fringes are usually inclined to the surface at a considerable angle, e.g. typically around 90°.

A "reflection" hologram is one where rays leave by the same surface at which incident rays enter. Fringes are usually substantially parallel to the surface of the holographic support medium.

"Edge-lit" holograms are ones where rays leave the hologram substrate or bulk of holographic support medium (e.g. glass plate) via a surface which is substantially 90° to that via which incident rays enter. Fringes are usually at an angle to the surface, typically of around 45°.

A "surface" hologram is one where the surface of a medium is contoured with an appropriate spatial amplitude and with a regularly spaced pattern so that it is capable of diffracting and/or reflecting light. This has the properties of another type of "phase" hologram by virtue of creating a path difference between diffracted and/or reflected rays arriving at a common point from each point on its surface. If such a surface is defined on a transparent medium then light transmitted through the medium is subjected to periodic phase changes across the surface due to the variation in optical path length imposed by the refractive index of the bulk of the medium.

The holographic support medium is one in which a hologram can be made and which is capable of exhibiting one or more of the properties of the sensitive mechanisms described below. The support medium preferably comprises a native or modified matrix with viscoelastic properties which alter as a result of an interaction with an analyte species.

For example, the matrix is formed from the copolymerisation of (meth)acrylamide and/or (meth)acrylate-derived comonomers. In particular, the monomer HEMA (hydroxyethyl methacrylate) is readily polymerisable and cross-linkable. PolyHEMA is a versatile support material since it is swellable, hydrophilic and widely biocompatible.

Other examples of holographic support media are gelatin, K-carageenan, agar, agarose, polyvinyl alcohol (PVA), sol-gels (as broadly classified), hydro-gels (as broadly classified), and acrylates. Further materials are polysaccharides, proteins and proteinaceous materials, oligonucleotides, RNA, DNA, cellulose, cellulose acetate, siloxanes, polyamides, polyimides and polyacrylamides. Gelatin is a standard matrix material for supporting photosensitive species, such as silver halide grains. Gelatin can also be photo-cross-linked by chromium III ions, between carboxyl groups on gel strands. These materials may also be used in combinations of two or more.

The polymer composition may be optimised to obtain a high quality film, suitable for the preparation of a reflection hologram. The film should allow for the production of a uniform matrix, in which holographic fringes can be formed.

Examples of analytes which may be identified and quantified by the invention include gases and liquids such as ions, metabolites, antigens/antibodies, glucose, oxygen, carbon dioxide, urea, ions, including protons (for pH detection), alcohols, sulphides, and lactates. This list of analytes is given by way of example only. It will be evident that other analyte species exist and can be identified using a suitable holographic sensor, in accordance with the present invention.

The invention may be used to detect an analyte in a bodily fluid, for example urine, blood or an optical fluid. A particular analyte of interest is glucose, whose levels in the eye are known to correlate with those in the blood. The invention thus may be used to monitor blood levels of glucose indirectly by monitoring the levels in an optical fluid such as tears.

There are a number of basic ways to change a physical property, and thus vary an optical characteristic. A combination of one or more of these may be employed to affect a change in the hologram and/or holographic support medium, so as to give rise to a change in a physical property of the holographic element. If any change occurs whilst the hologram is being replayed by incident broad band, non-ionising electromagnetic radiation, then an optical property varies and a colour or intensity change, for example, may be observed.

A physical property which may be varied is the modulation of complex index of refraction. This may be changed by chemical modification of the holographic element, in order to change one or more optical properties. For example, an enzyme can initially enhance the depth of the modulation of complex index of refraction by cleaving at sites in between fringes. Preferably, the sensor includes a holographic element comprising a medium containing a spatial distribution of modulated index of refraction, which can be modified by the addition of an analyte species, such that the spectral and/or directional nature of incident radiation is modified in dependence upon a variation in said spatial distribution of modulated index of refraction.

The holographic element may also be prepared so that its response to an interaction with an analyte is a temperature change. One or more dimensions of the holographic element, for example, will vary as a result of the temperature change. This results in a change in one or more optical properties.

The physical property that varies is preferably the size or volume of the support medium. This may be achieved by incorporating, into the support matrix, groups which undergo a reversible change upon interaction with the analyte, and cause an expansion or contraction of the support medium. The support medium may comprise a polymer or copolymer matrix, on or in which the groups are immobilised or present, e.g. in an interpenetrating network. An example of such a group is the specific binding conjugate of an analyte species. Imprinted polymers, or synthetic or biological receptors, may be used.

Another variation is in the active water, solvent or charge content of the support medium. In this case, the holographic support medium is preferably in the form of a gel.

Analyte molecules that can react with at least two functional groups in the element may form a reversible cross-link between separate parts of the support matrix, thereby altering the visco-elastic properties of the support matrix. Consequently, if present within a solvent-containing environment, and the support matrix changes, the support matrix contracts and the separation of the fringes is reduced. Specificity may be provided by ensuring that specific binding sites are provided within the gel matrix.

One parameter determining the response of such a system is the extent of cross-linking. The number of cross-linking points due to polymerisation of monomers should not be so great that complex formation between polymer and analyte-binding groups is relatively low, since the polymer film may become too rigid. This may inhibit the swelling of the support medium.

By way of example of a glucose sensor, for the continuous detection of glucose, a hydrogel-based hologram may have a support medium comprising pendant glucose groups and a lectin, preferably concanavalin A (con A). The lectin binds to the pendant glucose groups and acts as a cross-linker in the polymer structure. In the presence of freely diffusible glucose, the extent of cross-linking will decrease as glucose in solution displaces polymer-attached glucose from the binding sites on the lectin, resulting in swelling of the polymer. Volume changes in hydrogel films containing pendant glucose groups and con A can be observed using a reflection hologram. A volume change in the hydrogel alters the fringe separation of the holographic structure and can be followed as a shift in the peak wavelength of the spectral reflected response.

Water-based systems are preferred in such a holographic sensor, since they protect the lectin from exposure to organic solvents. Examples of suitable glucose components are high molecular weight dextran, and the monomers allylglucoside and 2-glucosyloxyethyl methacrylate (GEMA). Dextran, having no inherent polymerisable functionality, can be entrapped during the polymerisation of acrylamide-based monomers; allylglucoside and GEMA can be polymerised either individually or together with comonomers. The polymers are preferably prepared as thin films on glass supports.

A holographic glucose sensor can be constructed using any other suitable glucose receptor which allows a reversible change in a physical property of the support medium upon binding with glucose. For example, the support medium may comprise pendant boronate groups, such as phenylboronate. Two adjacent diol groups in glucose bind with a boronate group in a reversible condensation reaction. Thus in a holographic element, reaction of glucose with pendant boronate groups causes an expansion of the support medium, due to the size of glucose and its associated hydration shell. This expansion is observed as a shift in the reflectance maxima to longer wavelengths.

The continuous sensing of oxygen can be achieved by incorporating groups which reversibly bind oxygen into the holographic support medium. Example of suitable groups are complexes of a transition metal such as cobalt, nickel, iridium or ruthenium, e.g. complexes such as $Ir(PPh_3)_2(CO)Cl$ ("Vaska's complex"), tetracyanocobaltates, and porphyrin ring complexes, in particular the haem proteins haemoglobin and myoglobin. These groups can be immobilised onto the polymer matrix of the support medium. Upon binding with oxygen, these groups undergo a conformational shift resulting in an expansion of the hologram. This expansion is detected optically as a shift in wavelength.

Similar conformational shifts occur for macrocyclic groups such as crown ethers, which reversibly bind a range of ionic species. Crown ethers are well known to reversibly bind Group I and Group II metal ions. Therefore a crown ether which is specific to an ionic analyte can be immobilised in the support medium and used to continuously monitor the presence of the analyte.

The following Examples illustrate the invention, in conjunction with the accompanying drawings.

EXAMPLE 1

Detection of Glucose

A monomer mixture of 0.36 g acrylamide, 0.42 g methacrylamide, 0.35 g N,N-dimethylacrylamide, 1 ml water, 40 μl 5% DMPA, 0.03 g methylene bis-acrylamide, and 0.1 g vinylphenylboronic acid was adjusted to pH 9 by addition of aqueous NaOH, and subsequently polymerised. Silver was added to the resulting polymer using 0.2M $AgNO_3$ dissolved in 5% acetic acid. The hologram was then recorded in 20% methanol and developed in a standard developer; such developers are detailed in Practical Holography by Graham Saxby, published by Prentice Hall.

Detection of glucose was made in the presence of a 0.1 M phosphate buffer with 0.1 M NaCl solution at various pH values. The hologram was placed in 1 ml of buffer with a stirrer, and 20 ml of glucose in water (which had been left for 24 hours) was added to the buffer to a glucose concentration of 2 mM.

Readings were taken at 30 second intervals for a range of pH values. The system was reversible at all pH values (including physiological pH values) tested.

Figure 2:
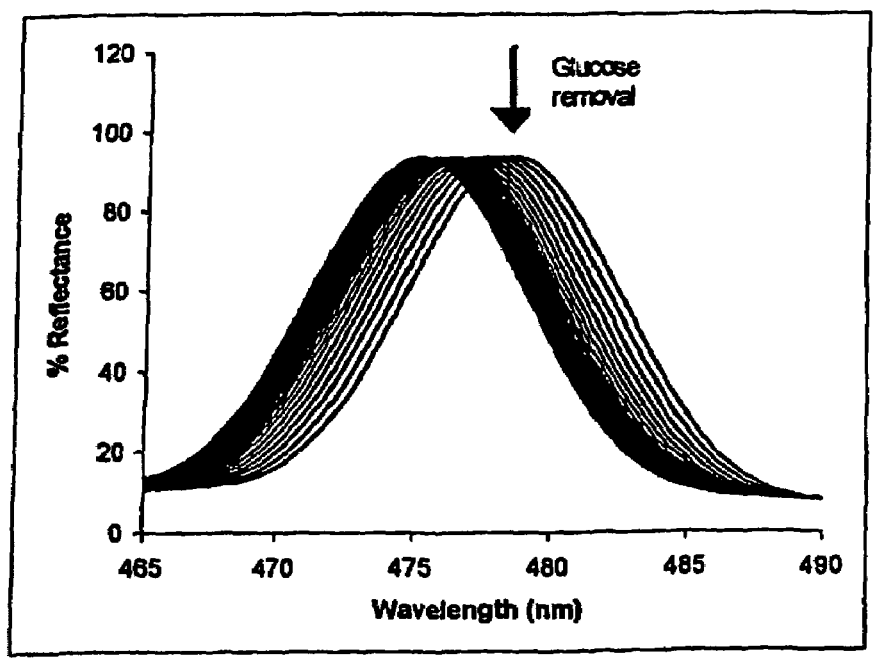

For example, at pH 8.1, addition of glucose resulted in expansion of the polymer, with most of the expansion taking place within 5 minutes of glucose addition. This expansion was observed as a reduction in the wavelength of reflection, as shown in FIG. 1. After rinsing twice with buffer, the hologram contracted, reverting to its original conformation; the wavelength returned to its original value, as shown in FIG. 2.

EXAMPLE 2

Detection of Oxygen Using "Vaska's Complex"

"Vaska's complex" was immobilised onto a plain HEMA hologram by evaporation from solution in chloroform (2 ml of 5 mg/ml solution). The hologram was then sparged with oxygen in a nitrogen-saturated buffer (50 mmol phosphate buffer, pH 7.0).

Figure 3:
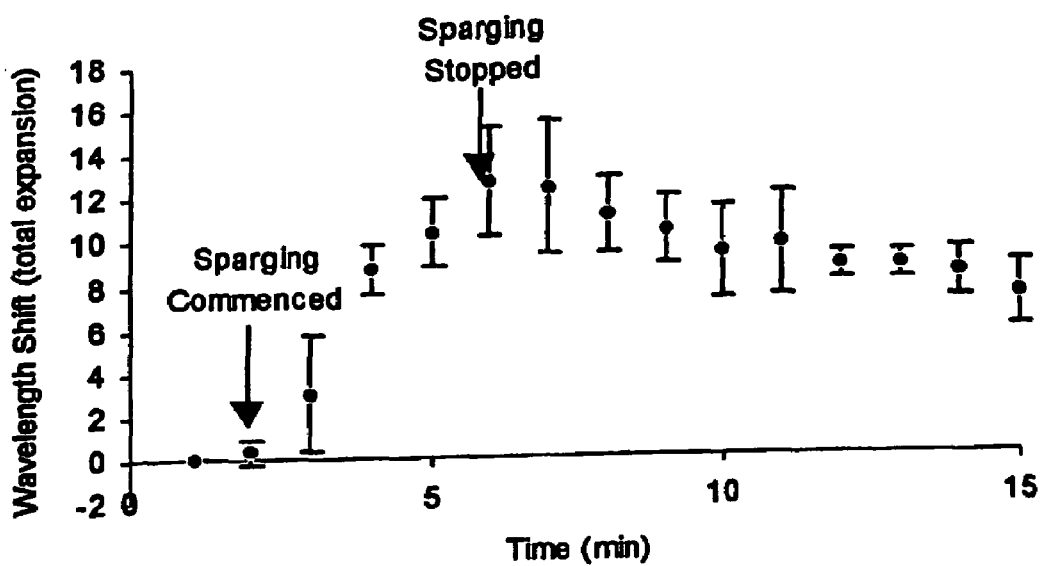

Upon sparging with oxygen, a small, reversible expansion occurred, resulting in an increase in wavelength of about 10 nm relative to controls. This wavelength shift is shown in FIG. 3. After sparging ceased, a proportion of the bound oxygen molecules underwent the reverse reaction and the holographic medium contracted slightly. This was observed as a slight reduction in wavelength.

EXAMPLE 3

Detection of Oxygen Using Oxygen-binding Proteins

A holographic sensor was produced by immobilising haemoglobin onto a HEMA polymer by drying, followed by the addition of 1.5% acidified glutaraldehyde for 3 minutes. A holographic sensor comprising immobilised myoglobin was similarly produced.

Figure 4:
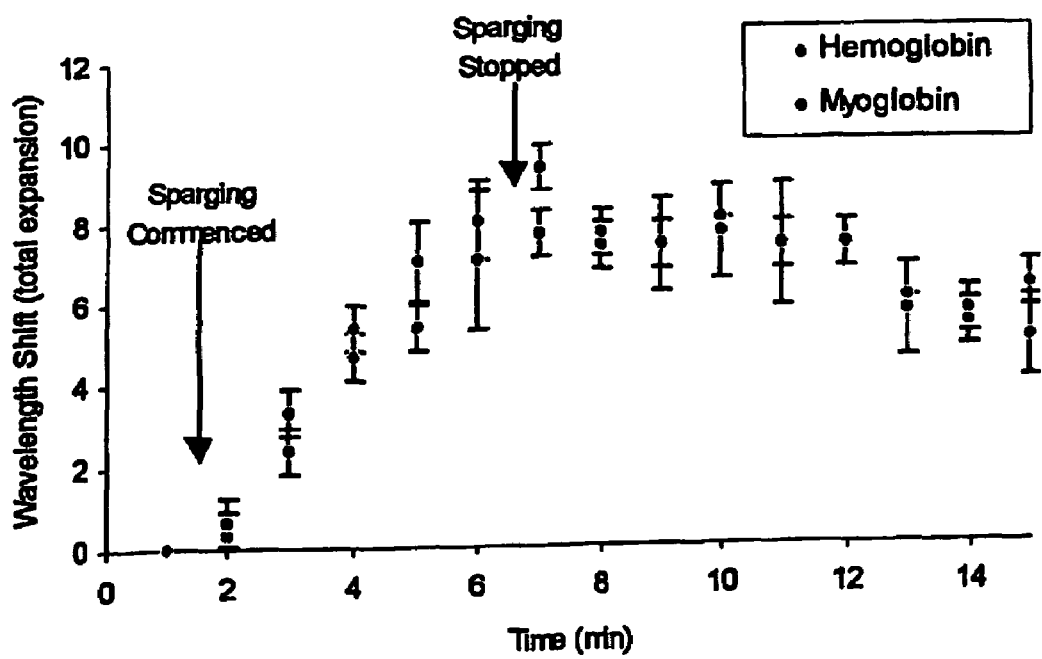

The holograms were sparged with oxygen for approximately 5 minutes. As can be seen from FIG. 4, a response to changing oxygen concentration was displayed by both haemoglobin and myoglobin containing holograms.

EXAMPLE 4

Detection of pH

Figure 5:
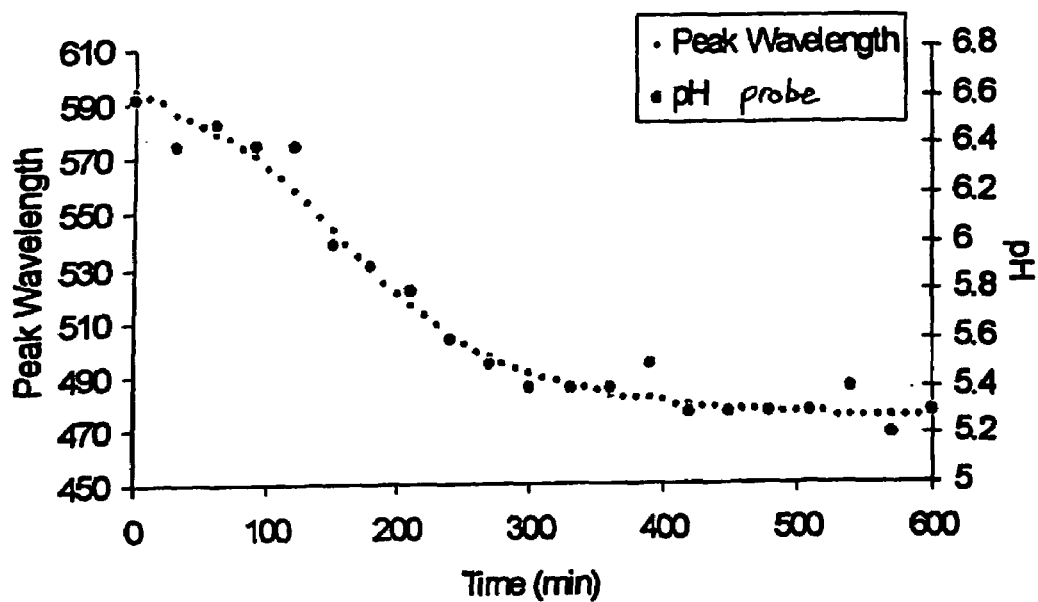

Holograms comprising a polymer content of 8% methacrylic acid (MAA) were used to monitor the pH in *Lactobacillus casei* cultured in MRS broth. As the *lactobacillus* grew and produced lactic acid the hologram contracted rapidly in response to the fall in pH. This was observed as a shortening of the peak wavelength of reflection of the hologram during the fermentation, as shown in FIG. 5.

When the peak wavelength of reflection of the hologram was compared with pH determined by a pH probe, a precise correlation was found, with less 'scatter' associated with the hologram than the pH probe.

Similarly, holograms comprising 4% DMAEM (dimethylaminoethyl methacrylate)-HEMA were used to continuously monitor *Escherichia coli* cultures, which also produce acid upon expansion. Peak wavelength of reflectance of the holograms correlated closely with pH.

Figure 6:
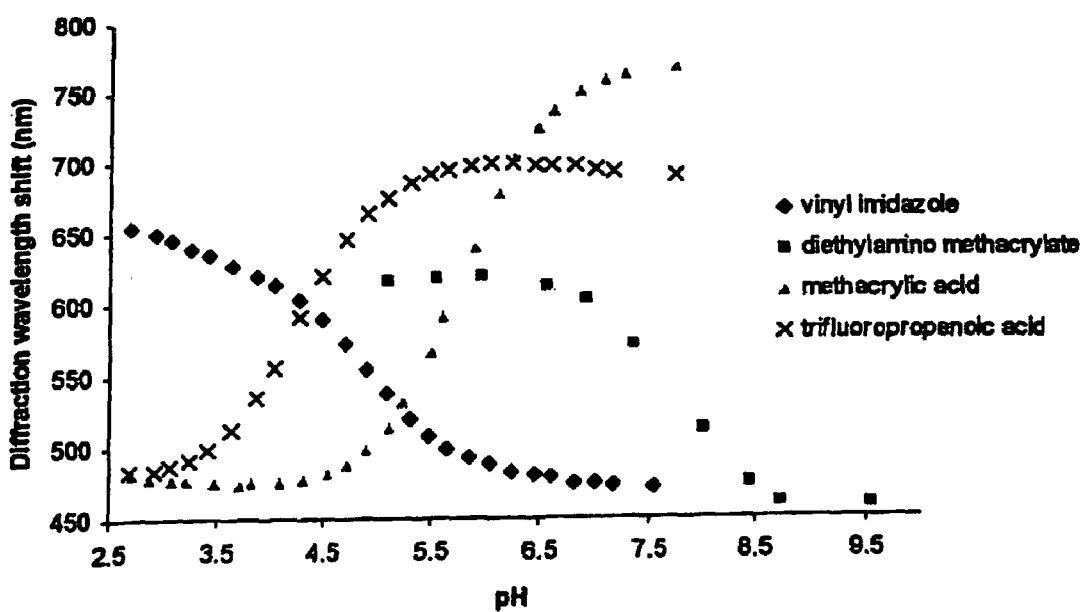

FIG. 6 shows the pH sensitivity of four different holographic sensors, wherein each sensor comprises a copolymer formed from HEMA and a pH-sensitive comonomer. In this example, the pH-sensitive comonomers used were vinylimidazole, diethylaminomethacrylate, methacrylic acid and trifluoropropenoic acid. The pH sensitivities are markedly different, showing how a polymer composition may be optimised for greater sensitivity over a specific pH range.

The following Examples 5-7 illustrate the invention using 3 cyclodextrine (CD) derivatives to make sensors.

EXAMPLE 5

Cyclohexaamylose "Alpha CD"

1 g alpha CD (dried) dissolved in 5 ml dry DMF and 3 ml dry triethylamine. Flask then chilled in ice bath. 2.7 ml methacryloyl chloride then added slowly to the stirred mixture in 100 microliters (μl) increments over 10 minutes. The flask stoppered with $CaCl_2$ drying tube, was left stirring at room temperature overnight. The mixture was then shaken with 100 ml toluene and the solvent was filtered off by Buchner funnel/water pump. The precipitate was then shaken with 100 cc acetone and again filtered and finally rinsed with 50 cc acetone and dried.

The methacrylated product was then stored in a dark bottle labelled alpha CD-M.

A "smart" polymer was then made as follows: 60 mg alpha CD-M was dissolved in 150 ul methanol.

The following were then added in order and each component dissolved before adding the next.
5 mg DMPA
125 μl HEMA
10 μl EDMA The solution was then coated on microscope slides and polymerized under UV light as previously described. (Alternatively the polymerization could be carried out thermally at around 60° C. for several hours if the DMPA was substituted by AIBN)

Holographic gratings were then made in the slides using the diffusion method as previously described.

EXAMPLE 6

Cycloheptaamylose or Beta-CD 1 g beta-CD (dried) dissolved in 5 ml dry DMF and 3 ml dry triethylamine. Flask then chilled in ice bath.

2.5 ml methacryloyl chloride then added slowly to the stirred mixture in 100 μl increments over 10 minutes.

The flask stoppered with $CaCl_2$ drying tube, was left stirring at room temperature overnight.

The mixture was then shaken with 100 ml toluene and the solvent was filtered off by Buchner funnel water pump. The precipitate was then shaken with 100 cc acetone and again filtered and finally rinsed with 60 cc acetone and dried.

The methacrylated product was then stored in a dark bottle labelled beta CD-M.

A "smart" polymer was then made as follows: 60 mg beta CD-M was dissolved in 150 μl methanol.

The following were then added in order and each component dissolved before adding the next.
5 mg DMPA
125 μl HEMA
10 μl EDMA The solution was then coated on microscope slides and polymerized under UV light as previously described. (Alternatively the polymerization could be carried out thermally at around 60° C. for several hours if the DMPA was substituted by AIBN)

Holographic gratings were then made in the slides using the diffusion method as previously described.

EXAMPLE 7

Hydroxypyropyl Cylcooctaamylase or HP Gamma CD 1 g HP gamma CD (dried) dissolved in 5 ml dry DMF and 3 ml dry triethylamine.

Flask then chilled in ice bath.

2.5 ml methacryloyl chloride then added slowly to the stirred mixture in 100 μl increments over 10 minutes.

The flask stoppered with $CaCl_2$ drying tube, was left stirring at room temperature overnight.

The mixture was then shaken with 100 ml toluene and the solvent was filtered off by Buchner funnel/water pump. The precipitate was then shaken with 100 cc acetone and again filtered and finally rinsed with 50 cc acetone and dried.

The methacrylated product was then stored in a dark bottle labelled HP gamma CD-M.

A "smart" polymer was then made as follows: 60 mg HP gamma CD-M was dissolved in 150 μl methanol.

The following were then added in order and each component dissolved before adding the next.
5 mg DMPA
125 μl HEMA
10 μl EDMA The solution was then coated on microscope slides and polymerized under UV light as previously described. (Alternatively the polymerization could be carried out thermally at around 60 C. for several hours if the DMPA was substituted by AIBN)

Holographic gratings were then made in the slides using the diffusion method as previously described.

Figure 7:
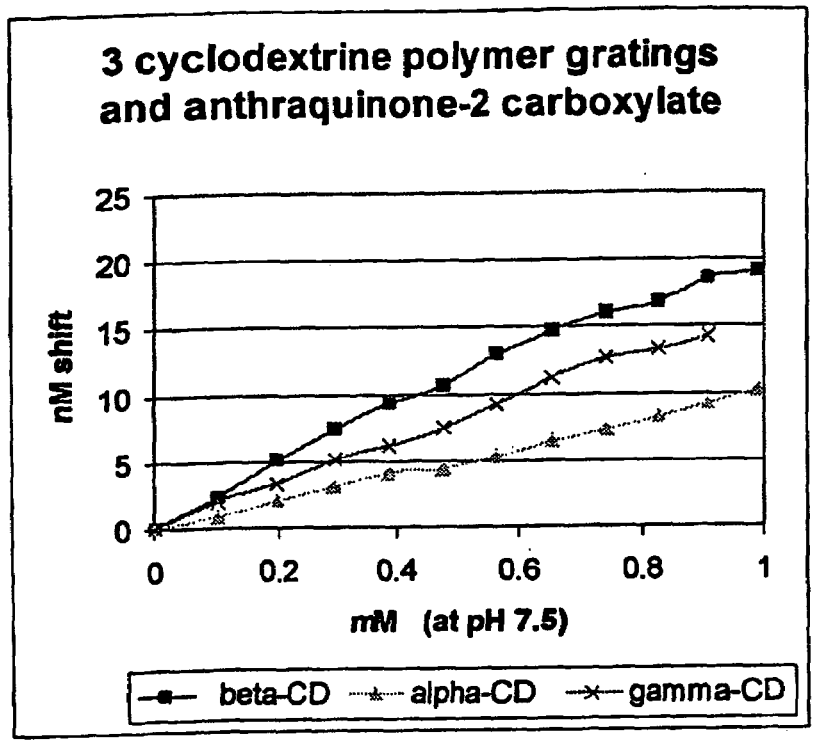
Figure 8:
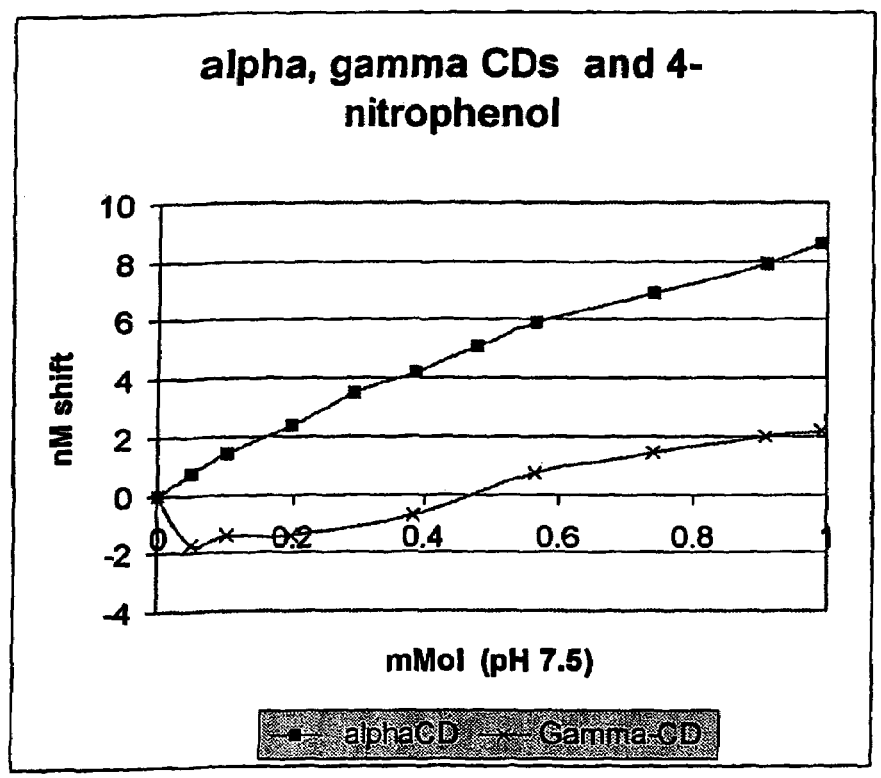

The effect of CD cavity size with respect to analyte molecule size can be seen in FIGS. 7 and 8.

EXAMPLE 8

This Example illustrates continuous monitoring of alcohol production by *Saccharomyces cerevisiae* using an alcohol sensor hologram.

Alcohol production by *S. cerevisiae* in grape juice was monitored over 24 hours using an alcohol sensor hologram.

Exponential phase *S. cerevisiae* cells growing in white grape juice were spun down, re-suspended in 20% glycerol and frozen. Cell density was determined by a viable count to be $8 \times 10^6$ $ml^{-1}$.

Figure 9:
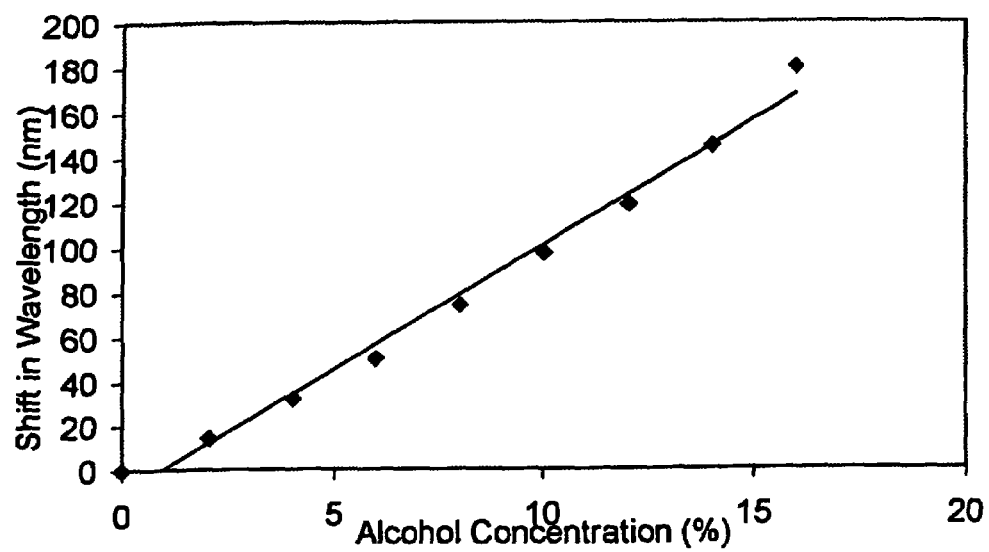
Figure 10:
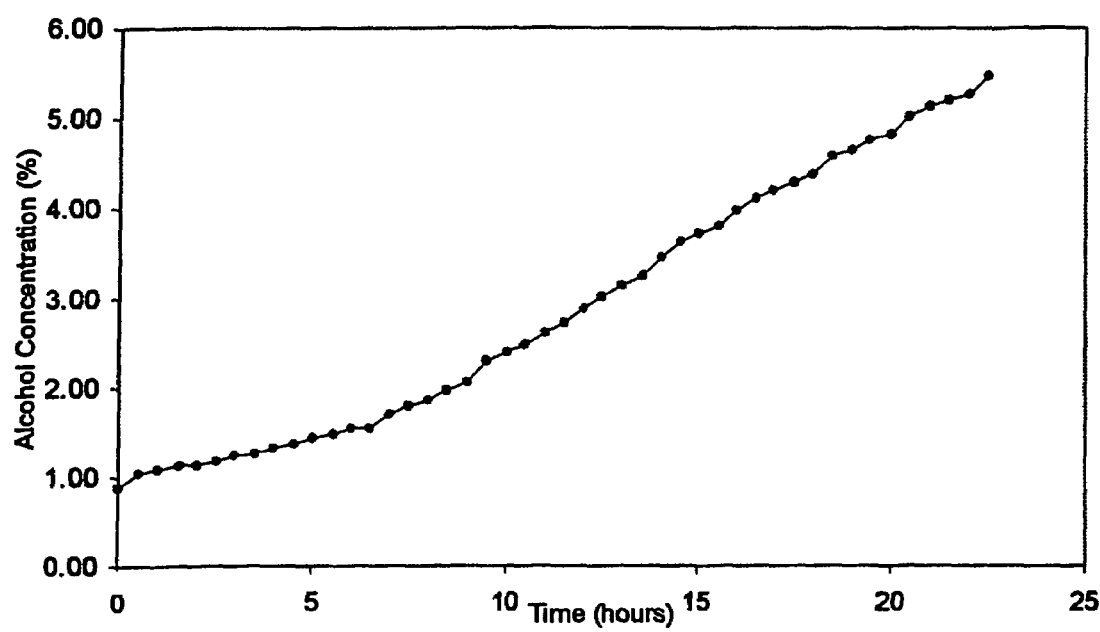

0.5 ml of seed culture was added to 2.5 ml of white grape juice in a cuvette and cultured at 30° C. for 24 hours. Alcohol (ethanol) production during this period was monitored using a polyHEMA alcohol sensor hologram, the peak wavelength of reflection at each time interval compared with a calibration produced using ethanol and grape juice (FIG. 9). Ethanol production during 24 hours of culture is shown in FIG. 10.

The invention claimed is:

1. A method for the detection of an analyte in a fluid, which comprises passing the fluid continuously over a holographic element comprising a medium and a hologram disposed throughout the volume of the medium, wherein an optical characteristic of the element changes as a result of a variation of a physical property occurring throughout the volume of the medium, wherein the variation arises as a result of interaction between the medium and the analyte, and wherein the reaction and the variation are reversible; and detecting any change of the optical characteristic.

2. The method according to claim 1, wherein the physical property is the size of the medium.

3. The method according to claim 1, wherein the optical characteristic is the reflectance, refractance or absorbance of the holographic element.

4. The method according to claim 1, wherein any change of the optical characteristic is detected as a color change.

5. The method according to claim 1, wherein any change of the optical characteristic is detected as an intensity change.

6. The method according to claim 1, wherein the analyte is glucose or lactate.

7. The method, according to claim 6, wherein the fluid is an optical fluid.

8. The method according to claim 1, wherein the analyte is $CO_2$ or oxygen.

9. The method according to claim 1, wherein the fluid is an optical fluid.

10. A device for the detection of an analyte in a fluid, which comprises a fluid conduit having an inlet, an outlet, and a holographic element, which comprises a medium and a hologram disposed throughout the volume of the medium, over which the fluid can flow, wherein the device also includes a window whereby non-ionising radiation can irradiate the holographic element, and wherein the analyte is detected by contacting the fluid with the holographic element, wherein an optical characteristic of the element changes as a result of a variation of a physical property occurring throughout the volume of the medium, wherein the variation arises as a result of interaction between the medium and the analyte, and wherein the reaction and the variation are reversible.

11. The device, according to claim 10, wherein the physical property is the size of the medium.

12. The device, according to claim 10, wherein the optical characteristic is the reflectance, refractance or absorbance of the holographic element.

13. The device, according to claim 10, wherein any change of the optical characteristic is detected as an intensity change.

14. The device, according to claim 10, wherein any change of the optical characteristic is detected as an intensity change.

* * * * *